US008591415B2

(12) United States Patent
Klinke et al.

(10) Patent No.: US 8,591,415 B2
(45) Date of Patent: Nov. 26, 2013

(54) CHILD-FRIENDLY ANALYTE MEASUREMENT INSTRUMENT

(75) Inventors: Martin Klinke, Halle (DE); Dieter Hofmann, Halle (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 739 days.

(21) Appl. No.: 12/580,317

(22) Filed: Oct. 16, 2009

(65) Prior Publication Data

US 2010/0121162 A1 May 13, 2010

(30) Foreign Application Priority Data

Oct. 16, 2008 (EP) ..................................... 08166805

(51) Int. Cl.
*A61B 5/00* (2006.01)

(52) U.S. Cl.
USPC ........................................................ 600/309

(58) Field of Classification Search
USPC ........................................................ 600/309
See application file for complete search history.

(56) References Cited

U.S. PATENT DOCUMENTS 6,165,035 A  12/2000  Avner
7,223,103 B2 *  5/2007  Cantrell et al. ............... 434/265
2002/0000062 A1 *  1/2002  Smirnov ......................... 44/397
2005/0004437 A1  1/2005  Kaufmann et al.
2005/0017646 A1  1/2005  Boulos et al.
2005/0176461 A1  8/2005  Bozzone et al.
2006/0040333 A1 *  2/2006  Zocchi ............................ 435/14
2008/0015422 A1 *  1/2008  Wessel .......................... 600/301
2008/0220688 A1 *  9/2008  Cuisinier ........................ 446/73

FOREIGN PATENT DOCUMENTS

WO      03/034912 A1    5/2003
WO   2008/037061 A1    4/2008

* cited by examiner

*Primary Examiner* — Rodney Fuller
(74) *Attorney, Agent, or Firm* — Krieg DeVault LLP

(57) ABSTRACT

Embodiments of a child-friendly analyte measurement system are provided for detecting at least one analyte in a bodily fluid. A measurement system comprises at least one measurement instrument for detecting the analyte in the bodily fluid. The measurement instrument is configured as a portable hand-held instrument and has a housing with at least one display element. Furthermore, the measurement system comprises a toy, in particular a figurine or a toy animal. The toy has at least one receptacle for reversibly holding the measurement instrument, which receptacle is configured such that if the measurement instrument is held by the receptacle, the display element is accessible, at least in part. The measurement instrument is configured such that it can be used both in the measurement system and also, optionally, independently of the toy. Further aspects include a kit, a method, and the toy for the provided measurement system.

20 Claims, 12 Drawing Sheets

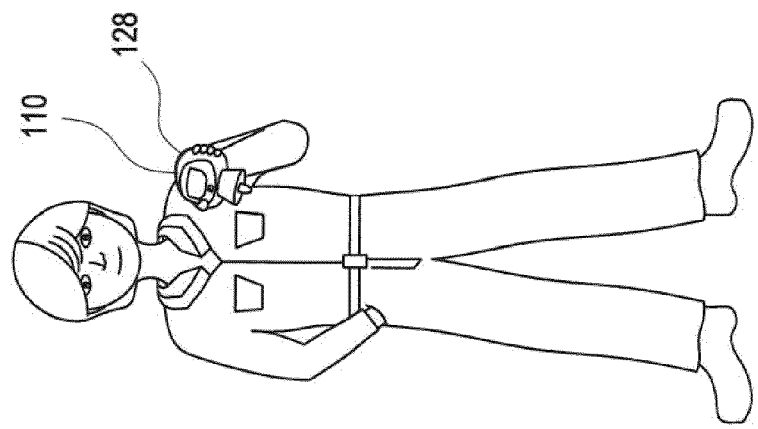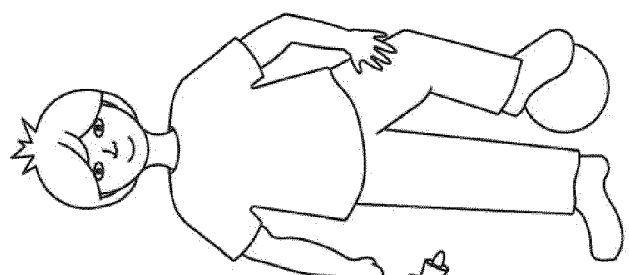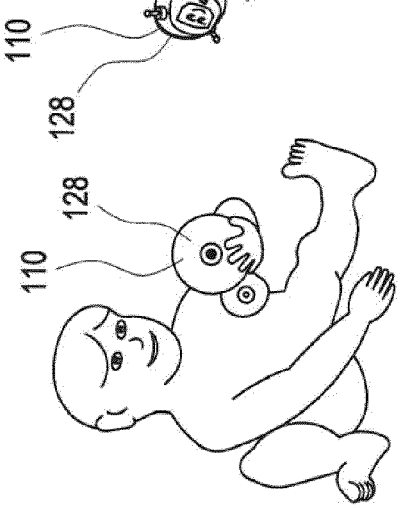
Fig. 3

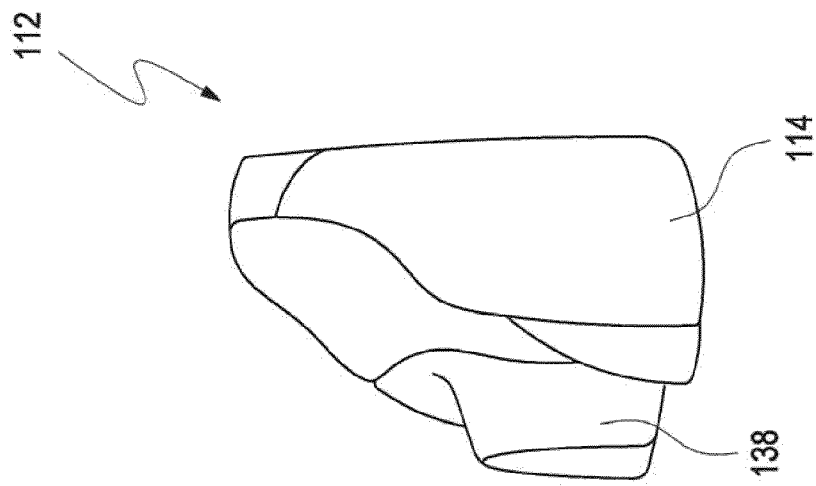
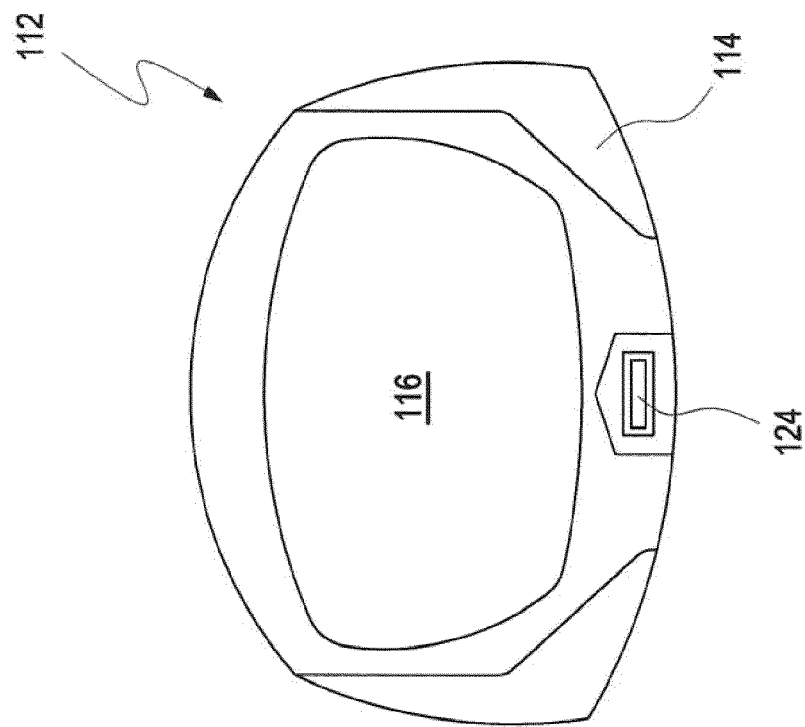
Fig. 4 B
Fig. 4 A

CHILD-FRIENDLY ANALYTE MEASUREMENT INSTRUMENT

CLAIM OF PRIORITY

The present application is based on and claims priority to European Patent Application 08166805.5, filed Oct. 16, 2008, which is hereby incorporated by reference in its entirety.

TECHNICAL FIELD OF THE INVENTION

The present invention relates to a measurement system for detecting at least one analyte in a bodily fluid, and more particularly to a toy, such as a toy animal, which can be used in the measurement system in order to make the system more child-friendly, and a kit for detecting at least one analyte and a method for producing a measurement system for detecting at least one analyte in a bodily fluid. An exemplary field of use for such measurement systems, toys, kits and methods is measurement of blood glucose. However, other fields of use are also possible.

BACKGROUND

In many cases, qualitative and/or quantitative detection of different analytes in bodily fluids of a human or animal patient are required for health protection and monitoring and treating different types of diseases. The present invention relates to in particular the monitoring of blood glucose. However, the invention can additionally or alternatively be used in different fields as well, for example for the qualitative and/or quantitative detection of different types of analytes. For example, it is possible for cholesterol and/or lactate to be detected, or coagulation measurements can be carried out. It is also possible for different types of bodily fluids to be used instead of blood, such as urine or interstitial fluid. The invention will be described in the following text using the example of blood glucose measurement, without restricting possible additional embodiments and fields of application.

In order to detect the analyte, measurement instruments are used in many cases which detect the analyte using test elements. These test elements can for example be available in the form of test strips, test bands, test discs, foldable test elements or in another form and can for example be designed as multi-use or single-use test elements (disposables). In addition to measurement instruments which utilize individual test strips, measurement instruments are known which operate using a number of stored test elements. By way of example, the at least one analyte is detected electrochemically and/or using optical measurement methods. In general, the test elements have at least one test field with test chemicals which change at least one detectable physical and/or chemical property when the at least one analyte is present. A large number of measurement methods, test elements and measurement instruments are known; it is also within the scope of the present invention to make use of these.

Diabetes monitoring in the field of so-called "home monitoring" can require up to seven measurements daily. So as not to unnecessarily limit the daily routine of the patient due to these measurements, the measurement instruments are generally configured as portable measurement instruments, and therefore these can, for example, be taken to work or leisure-time activities by a patient. Since the required measurements often have to be made with a prescribed regularity, a significant amount of discipline is nevertheless necessary to be able to ensure complete monitoring.

However, taking such care and discipline are not a matter of course, but have to be learnt and in most cases are the result of diligent upbringing. A small, but nevertheless non-negligible patient group in the field of diabetes monitoring are children and minors, particularly in the case of Type I diabetes, but in increasing numbers in the case of Type II as well. However, particularly in the case of children and adolescents, it is particularly difficult to encourage these patients to measure regularly.

It is for this reason that the prior art discloses systems which are designed specifically for patients in infancy. In one such system, a simulation apparatus is provided for playfully evaluating and displaying blood glucose values. Such an evaluation uses a virtual creature which is illustrated on a display. This virtual creature can communicate with the user in a number of ways. By way of example, the housing of the simulation apparatus can be designed in the form of a teddy bear. See, e.g., WO 03/034912 A1.

However, such instruments tailored specifically to patients in their infancy have significant disadvantages in practice. Here, reference is made in particular to the cost pressure in the health sector which has increased significantly in recent years. As a result of this cost pressure, measurement instruments must generally be produced virtually cost-neutrally. However, the mentioned child-specific instruments have to be produced specifically and separately for a relatively small number of patients. Even amongst these patients, it is not possible to use uniform instruments, since the instruments have to be adapted in their outer appearance and/or in their software, depending on the addressed age of the patient.

It can clearly be seen that the known specially-made products for a small number of clients are connected with significant complexity regarding production, storage and logistics. Furthermore, it has to be noted that the design of products destined for children or adolescents is subject to a high degree to fashion trends; the media, for example, promote this even more. Hence, the appearance of the measurement instruments does not only have to be adapted to certain ages, but also to such fashion trends, in order to maintain the interest of the children and the adolescent patients. These difficulties overall have lead to the situation where measurement instruments suitable for children have until now not been able to assert themselves on the market in relatively large numbers.

It is therefore an object of the present invention to provide a measurement system which avoids the disadvantages of known measurement systems. In particular, the measurement system is intended to make measurements suitable for children possible and nevertheless be able to be produced cost-effectively in large volumes.

SUMMARY

This object is achieved by a measurement system, a toy, a kit and a method with the features of the independent claims. Advantageous developments of the invention, which can be implemented on their own or in combination, are illustrated in the dependent claims. A first aspect of the present invention proposes a measurement system for detecting at least one analyte in a bodily fluid. As illustrated above, the measurement system will mainly be described in the following text with reference to detecting blood glucose. However, in principle, measuring different types of analytes and/or use with different types of bodily fluids is also conceivable.

Accordingly, in one embodiment, a measurement system comprises at least one measurement instrument for detecting the analyte in the bodily fluid. The measurement instrument is configured as a portable hand-held instrument and has a housing with at least one display element. Here, a measurement instrument is in general understood to be a measurement instrument which can qualitatively and/or quantitatively detect the at least one analyte in the bodily fluid. In particular, it can be one of the measurement instruments described above, that is to say a measurement instrument with a measurement function by means of which the analyte can for example be detected electrochemically and/or optically. In particular, the measurement instrument, as described herein, can operate using at least one test element, with all types of known test elements being usable in principle. With regard to this, reference can for example be made to the prior art.

In general, a display element is understood to be an element which is configured to convey at least one item of information to a user and/or patient. By way of example, this can be an optical item of information and/or an acoustic item of information and/or a haptic item of information. However, other types of information and/or combinations of the specified information and/or other types of information can also be used in principle. In one embodiment, the display element is configured as an optical display element.

In order to design the measurement system to be suitable for children, the measurement system furthermore comprises at least one toy. In principle, this toy can have any design and can in particular comprise a figurine and/or a toy animal, such as a stuffed animal, or be designed as such a toy animal. In general, the toy can be designed as a figure, in particular as a human figure, as an animal figure or as a fantasy figure, that is to say as a being which—at least in the fantasy of a child—can be assigned its own character. Such a design as a figure eases the communication between the patient and the measurement instrument, since contact with a figure can generally be formulated more casually or less formally than with a machine. Additionally, this design at least partly removes the infant patient's fear of a measurement.

In order to avoid the above-described disadvantages of known instruments, it is proposed within the scope of the present invention to provide the toy with at least one receptacle. The measurement instrument should be held or be able to be held, at least reversibly, at least in part, in this receptacle. Reversible in this case should be understood to refer to a receptacle which makes it possible to insert and/or remove the measurement instrument with minimal manual intervention, such as by a patient. Here, the receptacle should be configured such that if the measurement instrument is held by the receptacle, at least the display element of the measurement instrument is accessible, at least partially. Furthermore, it is also possible for further regions and/or elements of the measurement instrument to be at least partially accessible.

In the process, the measurement instrument, in particular as a result of the corresponding design of the housing, is configured such that the measurement instrument can be used both in the measurement system and also, optionally, independently of the toy or the measurement system. In this respect, it is proposed that the measurement system in particular uses commercially available measurement instruments which can be used independently of the measurement system. This use of an independent measurement instrument can in particular be ensured by the housing of the measurement instrument being configured such that it satisfies the requirements of a housing of a portable measurement instrument. By way of the example, the housing can ensure mechanical stability which makes it possible to carry along the measurement instrument independently of the toy, in e.g. a pocket, or else without a cover, without there being mechanical damage to the measurement instrument in usual conditions. The housing can also ensure protection against humidity and/or impurities. In this respect, the measurement instrument can, for example, be a conventional, commercially available measurement instrument.

The inventive design of the measurement system having the measurement instrument and the toy with a corresponding receptacle offers a number of advantages compared to known instruments with a design which is suitable for children. For example, in embodiments or the present measurement system, unlike prior art systems, the outer cover of the measurement instrument itself is not designed as a toy, but the measurement instrument is reversibly held in such a toy by means of a suitable receptacle. This affords the possibility of at the same time offering the measurement instrument without the toy to adult clients, without having to effect changes on the measurement instrument itself. It follows that the invention affords the possibility of undertaking an individual adaptation of a measurement instrument, e.g. a blood sugar measurement instrument, which is suitable for children without having to carry out changes in the analysis system itself.

Accordingly, the production of such measurement systems is simplified significantly. Hence, a method for producing a measurement system for detecting at least one analyte in a bodily fluid is proposed, in particular a measurement system in accordance with the above description and/or in accordance with one of the embodiments which will still be described in the following text. Accordingly, reference can be made to these optional embodiments for additional details. Here, a measurement instrument, for example a measurement instrument in accordance with the above description, is in turn used in the proposed method and can be utilized to detect the analyte in the bodily fluid. It is again proposed in particular to use a commercially available measurement instrument which is configured as a portable hand-held instrument and which can be used both in the measurement system comprising a toy and also, optionally, independently of such measurement system. The measurement instrument in turn has a housing with at least one display element. Furthermore, the proposed method uses a toy, such as a toy animal, with the measurement instrument being held reversibly in at least one receptacle of the toy. The receptacle is configured such that if the measurement instrument is held by the receptacle, the display element is accessible, at least partially.

In embodiments of a method according to the present invention, it is possible for a plurality of different types of toys to be stored in storage. By way of example, different toys can be stored for different age groups, as gender specific toys (e.g. figures, dolls and/or stuffed animals), for different regions, for different fashion trends or the like. The storage can be adapted according to the current preferences of the target group and can be updated without the measurement instruments having to be adapted for this purpose. It is then possible for a certain type of toy to be selected for the production of the measurement instrument during the production thereof, for example depending on the target group of the users.

Hence, the proposed measurement system and the proposed method make it possible for target-group specific measurement systems to be produced in a cost-effective manner, which measurement systems can be designed to be suitable for children and can also be adapted for current trends without much complexity. This makes it possible for costs to be cut significantly and for the production of specific equipment for a small number of clients to be avoided. Only relatively small adaptations can be effected if necessary, e.g. adaptations of the software of the measurement system. Examples of such adaptations, e.g. to change the character of a figure represented by the measurement system, are described below.

In addition to the measurement system and the production method, other embodiments of the present invention include a kit for detecting at least one analyte in the bodily fluid, such as for detecting blood glucose. The kit comprises a measurement instrument with the above-described features relating to a measurement instrument. In particular, it can once again be a commercially available measurement instrument. Furthermore, the kit comprises a number of toys, in particular figurines and/or toy animals, which respectively have at least one receptacle to hold the measurement instrument. With regard to further features of these toys, it is once again possible to refer to the above description and to the following possible refinements of such toys set out herein. This kit can for example be used in storage so as to quickly assemble a client-specific measurement system, for example according to the above or following description. However, such a kit can alternatively be used directly by a client, for example to arbitrarily change the appearance of the measurement system within the scope of toys contained in the kit. Thus, using one kit, a parent can for example provide individual measurement systems for a number of children, which measurement systems are adapted to the preferences of the respective child and which nevertheless are based on using the same measurement instrument. Thus, the kit can be used to produce a measurement system. This also makes it possible for costs to be reduced substantially since a number of users with different preferences can use the same measurement system.

Furthermore, in another aspect of the present invention, a toy is proposed, such as a figurine or a toy animal, which toy can be used in a measurement system according to the invention. The toy has at least one toy cover which substantially determines the outer shape of the toy. Furthermore, the toy comprises at least one receptacle for reversibly holding a measurement instrument for detecting an analyte in a bodily fluid, in particular a commercially available measurement instrument. The measurement instrument (such as is described herein) is configured as a portable hand-held instrument and has a housing with at least one display element. Here, the receptacle of the toy is configured such that if the measurement instrument is held by the receptacle, the display element is accessible, at least in part.

A toy designed in this fashion, which toy is specifically designed for use in a measurement system according to the invention as a result of the receptacle, can for example be distributed as an individual product, independently of the measurement instrument. By way of example, this makes it possible to react to changes in the preferences of the target group. For example, if the preferences of the children change, parents can react to these changed preferences by buying new, updated or changed toys. At the same time, producers can react to fashion trends by the independent distribution of such toys and therefore can update the outer appearance of the measurement system even though the design of the measurement instrument remains unchanged. This also makes it possible for significant cuts to be obtained in logistics.

As illustrated above, the display element can be configured as an optical display element and can, for example, comprise at least one display. However, alternatively, or additionally, different types of display elements are also possible. By way of example, it is possible for light-emitting diodes, luminous surfaces or similar types of optical display elements to be used. Furthermore, the measurement instrument can have additional elements which ensure interaction between user and measurement instrument. Thus, the measurement instrument can furthermore for example have at least one operating element, the receptacle being configured such that if the measurement instrument is held by the receptacle, the operating element is also accessible, at least in part. Here, "accessible" with regard to the display element is understood to mean that the provided, e.g. displayed, information can be perceived even if the measurement instrument is held in the receptacle. For example, a display cannot, or can only partly, be covered by the toy, e.g. by a toy cover. With regard to the operating elements, the term "accessible" means that the operation of these operating elements by the user or the patient is possible, at least in a restricted fashion but also without restrictions in some embodiments, even if the measurement instrument is held in the receptacle. The at least one operating element can for example comprise pushbuttons, knobs, keys or the like. Alternatively, or additionally, the at least one operating element can be wholly or partly combined with the display element, for example by using a touch screen on which, for example, virtual operating elements are displayed.

The receptacle can be adapted specifically to the measurement instrument. This adaptation can for example be effected by the receptacle having dimensions which are matched specifically to the dimensions of a certain type or a group of types of measurement instruments. Designing the receptacle for a number of types of measurement instruments is also feasible.

In order to fix the measurement instrument in the receptacle, the receptacle can furthermore, optionally, have at least one fixing apparatus which is configured to fix the measurement instrument relative to the toy. In particular, the toy can for example have an opening. This opening, with it analogously also being possible for provision to be made for a number of openings, can for example ensure access to the at least one display element and/or to the at least one operating element. Accordingly, an opening can be understood as being not only a completely uncovered opening, but, for example, openings are feasible which permit optical access and are correspondingly wholly or partly covered by a transparent material, e.g. a transparent plastic. This fixing apparatus can for example be configured to fix the measurement instrument such that the access through the at least one opening is maintained even during usual stress on a toy. In particular, this makes it possible to prevent shifting or tipping of the measurement instrument relative to the opening.

By way of example, the fixing apparatus can comprise a clamping apparatus, a screw apparatus, a rail or any other type of fixing apparatus which is conventionally used for fixing instruments and is known to a person skilled in the art. The fixing apparatus can interact with a corresponding fixing apparatus on the measurement instrument and can form a combined fixing apparatus. However, alternatively, fixing apparatuses can also be provided which do not require corresponding matching parts on the measurement instrument and so commercially available measurement instruments which are not specifically adapted to the measurement system can be used.

In one embodiment, the receptacle comprises a receptacle space in which the measurement instrument can be held at least partially. The receptacle can furthermore have at least one closing element which can also be wholly or partly identical to the fixing apparatus. This closing element can then be configured to secure the measurement instrument in the receptacle space when said closing element is in a closed state and to permit a removal of the measurement instrument from the receptacle when said closing element is in an opened state. In particular, the closing element can be configured such that opening and closing the closing element can also be effected by a user, in particular by a parent and/or a user in infancy. This makes it possible for the above-described advantages of the exchangeability of the toy in the measurement system to be ensured in a particularly simple fashion. This exchangeability can then be ensured not only during production, but, for example, also in daily use, in contrast to prior art systems herein described in which the outer appearance can in general only be changed by a person skilled in the art with appropriate tools. In particular, the closing element according to the invention can be configured such that opening and closing this closing element is possible without additional tools. By way of example, the closing element can comprise at least one of the following elements: a zipper; a pushbutton; a textile button; a lock which can be released by a user.

As illustrated above, the measurement instrument can in particular be configured to detect the analyte using at least one test element. All types of test elements known from the prior art can in principle be used within the scope of the present invention, e.g. the abovementioned test elements. Accordingly, the measurement instrument can for example have at least one application opening which is configured to enable a placement of a sample of the bodily fluid onto the test element. For example, this application opening can be configured such that a test element can be inserted into the application opening from the outside, e.g. an optical and/or electrochemical test element. Alternatively, or additionally, a test element held in the interior of the measuring instrument, e.g. in a test element repository, can also be moved out through the application opening and therefore a sample placement position of the test element becomes accessible to the user. Again alternatively, or additionally, the application opening can also be configured such that an application point on a test element is temporarily uncovered by this application opening such that the user can apply a corresponding liquid sample, e.g. a drop of blood. Different additional refinements are feasible. For example, the measurement system can be configured such that the sample can be placed when the measurement instrument is held in the receptacle. This can for example be ensured by the toy having at least one corresponding opening as illustrated above, which may be completely uncovered and/or which can be uncovered by a corresponding opening mechanism and which enables the application opening for the user even if the measurement instrument is held in the receptacle.

As already described above, in certain embodiments the toy is at least in part designed as a figure, that is to say as a being which—at least in the fantasy of a child—can be assigned its own character. Accordingly, the toy can for example be designed at least in part as a human figure, an animal figure or a fantasy figure. In one refinement, the receptacle has an opening, the opening being arranged at least in part in a facial region of the figure. By way of example, the opening can comprise a complete region of a face of the figure and/or only a partial region of the face, e.g. a region of the eyes and/or of the mouth. In other refinements, the opening is configured such that the display element can at least in part be recognized in the opening when the measurement instrument is held in the receptacle. This for example affords the possibility of parts of the face of the figure being displayed using a display of the display element. This makes it possible for the display element to complement the other appearance characteristics of the toy, in particular the figure. In embodiments in which the display element is configured as a variable display element, this affords the possibility of displaying e.g. the eyes and/or other components of the face which can also be designed to be able to change.

The measurement instrument can have a control which can, for example, be wholly or partly part of a central control of the measurement instrument but, however, can also be configured as an independent, decentralized control. This central control can, for example, wholly or partly control and/or monitor the above-described measurement objects for detecting the at least one analyte. By way of example, the central control and/or the control can comprise one or more data processing instruments, in particular one or more microcomputers. Furthermore, one or more storage elements can also be included.

The control can be configured to display at least parts of a face of the figure on the display element in at least one mode of operation. Here, the control can in particular be configured such that a facial expression of the face can be changed according to one or more conditions of the measurement instrument. Thus, a facial expression can for example comprise a design of the eyes and/or a mouth and/or other facial components. The facial expression can for example be changed according to one or more of the following conditions: according to a measurement result of the detection of the analyte in the bodily fluid; according to a time, in particular a time for a measurement to be carried out. However, alternatively, or additionally, an adaptation regarding further conditions of the measurement instrument is also possible. This makes it possible for a child user to be informed about the measurement results and the meaning thereof in a child-friendly manner, e.g. by a simple "good"-"bad" statement. A child-friendly, friendly reminder that a measurement should be carried out now can also be effected in this manner.

As described herein, the display element can be wholly or partly configured as an optical display element. However, the measurement instrument, in particular the display element, furthermore can also have further elements which make interaction with a user possible, for example elements that vibrate, emit acoustic signals or emit thermal signals. A combination of various interaction elements of this type or further interaction elements is also feasible. In one refinement, the measurement instrument, in particular the display element, furthermore has at least one acoustic element, the acoustic element being configured to output acoustic signals, in particular to output speech. Such an output of acoustic signals, in particular outputting speech, can for example further support the character of the illustrated figure of the measurement instrument, or it can be set according to the respective character. By way of example, a voice, choice of words, language or the like can be adapted to the respective character and/or the respective target group, again e.g. an age range, a country-specific target group, a gender-specific target group or the like. For example, the control can comprise a store which stores a number of modes with different language elements which can for example be selected according to the target group and/or, for example, according to the represented figure. The speech output can also comprise one or more of the abovementioned functions. In particular, at least one measurement result of the detection of the analyte in the bodily fluid can be output using the speech output. Alternatively, or additionally, it is also possible for a statement regarding at least one measurement result of the detection of the analyte in the bodily fluid to be output. Again, it is alternatively, or additionally, possible for there to be a request to undertake a measurement and/or a request to undertake at least one other action, in particular to exchange an energy store. A reply to a call by a user can also be emitted.

In addition, or as an alternative, to the at least one acoustic element which can emit acoustic signals, the measurement instrument can furthermore also comprise at least one input element for inputting acoustic signals. For example, this input element can comprise one or more microphones. Provision can be made for further building blocks, e.g. speech recognition modules, which can also for example be wholly or partly implemented in the control by software building blocks. This input element for inputting acoustic signals can for example be configured to input voice commands. This possible refinement can increase the impression of a child user that the measurement system is provided with its own character, and this can improve the interaction of a child patient with the measurement system. As an alternative, or in addition, to communication by means of keys and similar elements, there can be a more natural communication which can further increase the user-friendliness. Additionally, the refinement of the measurement system as a figure and the mentioned optional refinements which support the character of the figure can further reduce the inhibition threshold for a child user to use the measurement system. This makes it possible to in particular remove the child user's fear of the measurement to the greatest possible extent. Furthermore, it is possible that finding the measurement system is made easier, for example by a search call from the user and a corresponding reply by the measurement system. This also supports the child-friendliness of the measurement system since experience has shown that users in their infancy tend to be untidy, and there is a danger that a measurement system in the form of a toy cannot be found in the general untidiness of a play room.

As described above, the measurement instrument can also have at least one memory storage element, in particular volatile and/or non-volatile memory storage. Here, it is possible for a plurality of sets of character parameters from different types of toys to be stored in the memory storage element. For example, these can be character parameters from different types of figures. Here, character parameters are in general intended to be understood to be a set of parameters which are specifically adapted to a particular figure or other embodiment of the toy. For example, these can be voices of an acoustic output, facial expressions, languages or the like. According to the respective, specifically used toy, a certain set of character parameters can then be selected for the measurement system. This selection can for example be made possible by a menu, for example by a parent or by the child user. By way of example, if the toy is changed so that a different child can use the measurement system, a parent can then select a new set of character parameters which has been adapted for this specific toy. However, alternatively, or additionally, this selection can also be effected by the producer, for example within the scope of the above-described production method and/or within the scope of using the above-described kit.

The toy itself can be designed in a number of different ways and typically comprises, as described above, a toy cover which determines the outer shape of the toy. Here, the toy can be designed as a purely passive toy, without its own functions, such as movement functions and/or outputting acoustic and/or optical signals. However, alternatively, the toy can itself also be provided with at least one toy control, which in turn can for example comprise one or more data processing instruments and which can be configured to carry out at least one toy-specific function. For example, this toy-specific function can be a movement function of the toy and/or the output of acoustic and/or optical signals. However, alternatively, or additionally, other types of toy functions can also be controlled. This toy control, which can be configured independently of the measurement instrument and which can be used independently of the latter, can have at least one interface. By way of example, this interface can be a wired and/or wireless interface. This interface can be configured to interchange data and/or control commands with the measurement instrument, with it being possible for the toy control to be configured to communicate with a control of the measurement instrument. By way of example, this affords the possibility of transferring information regarding the type of toy to the measurement instrument. Hence, the measurement instrument can for example be configured to adapt at least one function to the respective toy used in accordance with the communication with the toy control. By way of example, this can, as illustrated above, be the selection of one or more sets of character parameters which can be matched specifically to the selected type of toy. However, alternatively, or additionally, it is also possible for e.g. a movement of the toy and/or an output of acoustic and/or optical signals to be coordinated between the toy and the measurement instrument.

As a generalization of this idea, the toy can have at least one identifier which has at least one item of information about the toy. Here, this at least one identifier can be configured in a number of different ways, such as by an electronic identifier, in particular as an electronic identifier which can be read out without being contacted. By way of example, the toy can have a radiofrequency chip (RFID chip) for this purpose which can be read out electronically without being contacted, e.g. by using a corresponding reader. Such readers are already contained in many measurement instruments so that no change of hardware is required in many cases of conventional measurement instruments. In principle, other types of identifiers are also possible. The at least one identifier can be configured independently of the optional toy control but can also be wholly or partly integrated in the toy control.

The at least one item of information about the toy can for example comprise at least one item of information about the type of the respective toy, for example an item of information about the figure embodied by the toy. The measurement instrument can be configured to read out the identifier, e.g. by using a corresponding reader. This read-out can be effected automatically, for example when the measurement instrument is inserted into the receptacle of the toy. This receptacle can also comprise an interface for communicating with the measurement instrument, e.g. a wireless and/or wired interface. This affords the possibility of transferring information, inter alia the information contained in the identifier for example, to the measurement instrument. Then the measurement instrument can in turn be configured, for example, to adapt at least one function to the information. Again, this adaptation can for example comprise the selection and/or adaptation of a set of character parameters. This makes it possible for a toy exchange to be automatically transferred to the measurement instrument so that no additional manual adaptation of the measurement instrument is necessary.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIG. 3 shows a symbolic illustration of the use of the measurement system for different age groups of children;

FIGS. 4A and 4B show a front and side view of an embodiment of a measurement instrument that can be used in one embodiment of the measurement system;

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
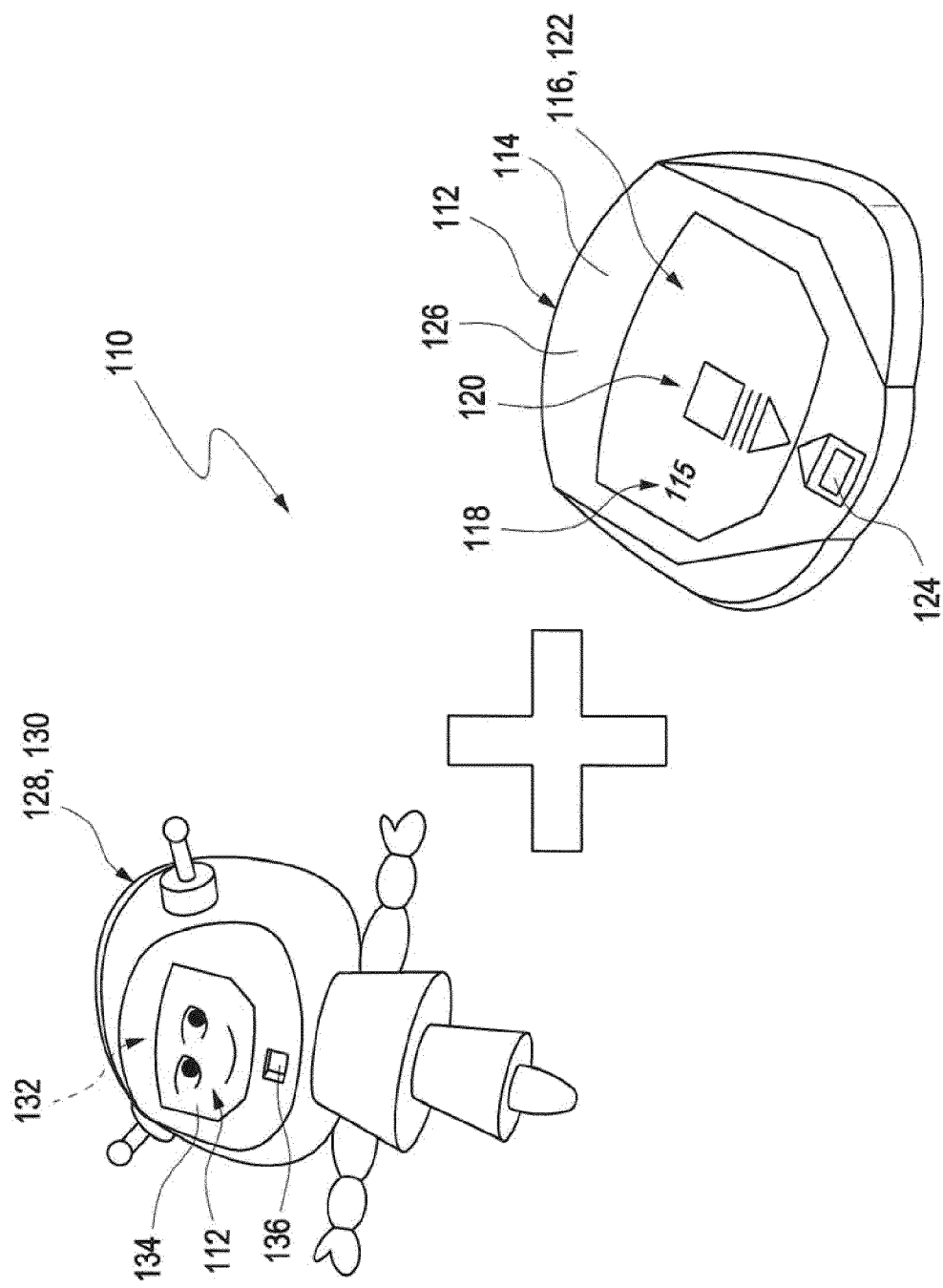
FIG. 1 shows a schematic illustration of a measurement system according to the invention including a measurement instrument and a toy.
Figure 2:
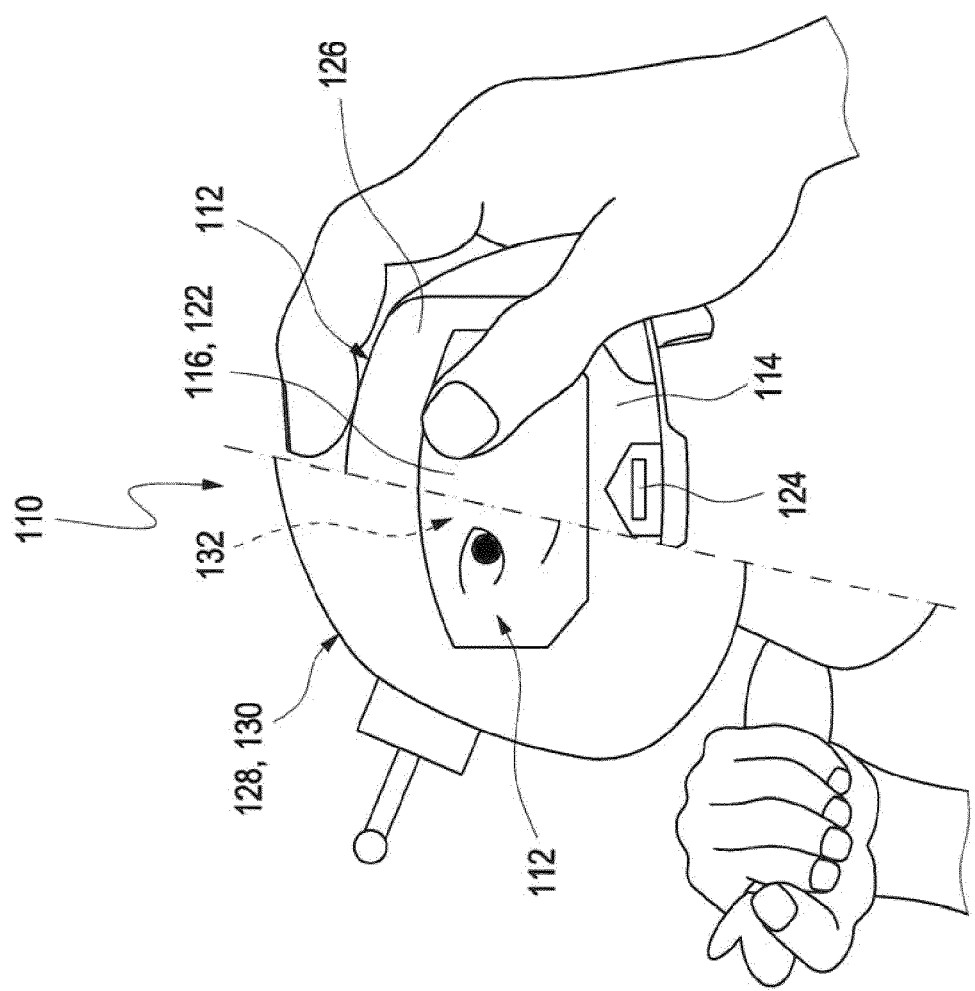
FIG. 2 shows a partial illustration of the measurement system and the measurement instrument as per FIG. 1.

Embodiments of a measurement system 110 for detecting an analyte in a bodily fluid according to the invention are shown in different views in FIGS. 1 and 2. In the following text, the exemplary presumption is made that the measurement system is configured to determine a blood glucose concentration, without intending to restrict further possible refinements.

To this end, in one embodiment the measurement system 110 comprises a measurement instrument 112 which is illustrated separately in the bottom right of the illustration as per FIG. 1. This measurement instrument 112 has a housing 114 which can, for example, be wholly or partly produced from stiff plastic. A multipart design of this housing 114 is also possible, for example a design with different plastics to improve e.g. the ergonomics of the measurement instrument 112. The housing 114 for example protects the interior space of the measurement instrument 112 from humidity and/or impurities, and protects from mechanical damages. The housing 114 allows the measurement instrument 112 to be also used independently of the described measurement system 110. By way of example, the measurement instrument 112 can correspond to a commercially available measurement instrument 112.

In one embodiment, the measurement instrument 112 has a display element 116. In the illustrated exemplary embodiment, this display element 116 is configured as an optical display element and for example comprises a display. Different types of displays can be used in the case, e.g. liquid crystal displays and/or organic light-emitting diode displays. The display element 116 can for example be used to display measurement values. In FIG. 1, these measurement values are symbolically referred to by reference symbol 118. However, in principle, other displays are also possible. Furthermore, it is for example also possible for usage instructions, which are referred to symbolically in FIG. 1 by reference symbol 120 and which for example can request the insertion of a test element (which is not illustrated in FIG. 1), to be displayed on the display element.

Furthermore, the measurement instrument 112 can additionally have one or more operating elements. These operating elements can be configured independently of the display element 116, but can however also be wholly or partly integrated in the display element 116. By way of example, the display element 116 can be wholly or partly configured as a touch screen, which is indicated symbolically in FIG. 1 by the reference symbol 122. By way of example, this affords the possibility of implementing a menu control or a different method for a user to input control commands and/or parameters into the measurement instrument 112.

In the illustrated exemplary embodiment, the measurement instrument 112 furthermore comprises an application opening 124. In the illustrated exemplary embodiment, this application opening 124 is arranged below the display element 116 on a front side 126. Arranging the application opening 124 on the front side 126, that is to say arranging it on the same side as the display element 116 and/or one of a number of display elements 116, simplifies the simultaneous access to the display element 116 and the application opening 124 when integrated in the measurement system 110. However, in principle, other refinements are possible.

By way of example, a test element, in particular a test strip, can be at least partly inserted into the measurement instrument 112 and/or can be at least partly removed from the measurement instrument 112 through the application opening 124. Usually, a test element of said type has an application point onto which the liquid sample is applied. Inserting the test element into the application opening 124, or removing the test element from the application opening, is generally effected such that this application point is exposed and so application of the liquid sample is possible.

The measurement instrument 112 can be a commercially available measurement instrument and therefore reference can be made in particular to the prior art for further possible refinements of this measurement instrument. However, the described embodiment is one embodiment within the scope of the measurement system 110 according to the invention.

The measurement instrument 112 is illustrated at the bottom right in FIG. 1 and in the partial image on the right in FIG. 2. Furthermore, the measurement system 110, as illustrated at the top left in FIG. 1 and in the partial image on the left in FIG. 2, comprises a toy 128. By way of example, this toy 128 can be a modified stuffed animal or, as illustrated symbolically in FIGS. 1 and 2, a figure in the form of a doll or a fantasy figure.

The toy 128 comprises a toy cover 130 which substantially determines the outer shape of the toy 128. Depending on the toy 128, this toy cover 130 can for example be produced from a hard and/or deformable, in particular flexible, material. Natural materials and/or artificial materials can be used for this purpose. In particular, material, color, shape, represented figure or any other manifestation of the toy cover 130 can be adapted to a particular target group, as explained in more detail below.

The toy 128 has a receptacle 132 which is only indirectly indicated in FIGS. 1 and 2 and which is wholly or partly located within the interior of the toy cover 130. Possible further details of this receptacle 132 will be explained in more detail in the following text, for example on the basis of FIGS. 5 and 6A and 6B. The receptacle 132 is configured such that if the measurement instrument 112 is held in the receptacle 132 then the display element 116 of the measurement instrument 112 is accessible, at least in part. For this purpose, the toy cover 130 can have one or more openings 134, 136 in the region of the receptacle 132, as indicated in FIG. 1. Thus, by way of example, it is possible for provision to be made for a first opening 134 which substantially corresponds to e.g. the area of the display element 116. Here, the opening can be completely open or, this should likewise be subsumed by the term opening, be covered in full or in part by a cover, such as a transparent cover, such that the optical information provided by the display element 116 can still be perceived by a user. The optional second opening 136 can, for example, be arranged in the region of the application opening 124 of the measurement instrument 112 such that insertion and/or removal of one or more test elements is possible through this opening 136. However, alternatively, or additionally, this second opening 136 can also be wholly or partly combined with the first opening 134. This second opening 136 is can be wholly or partly uncovered and/or can at least be uncovered using an opening mechanism such that the test element can be inserted and/or removed.

In FIG. 3, the adaptation of the measurement system 110 for the child user target groups is illustrated symbolically. In particular; this illustration shows how the outer appearance of the measurement system 110 can according to the invention be adapted to the different age groups of the users. While 1 to 3 year old infant users in general prefer simple toys 128 which might be produced from soft material and can generally be colored in pastel hues, users between the age of approximately 4 and 10 typically prefer toys 128 which represent figures with relatively pronounced character details. Here, for example, certain dolls, figures known from cinema, radio and television or the like are possible. By contrast, adolescents who are approximately 11 years old or older, by contrast— this is also indicated in FIG. 3 (right partial image)—prefer more complex toys 128 which can also, for example, deviate again from representing a figure or which can also be adapted to known figures from cinema, radio and television. All measurement systems 110 in FIG. 3 can be based on the same measurement instrument 112, with only the toy cover 130 or the toy 128 having to be replaced. Thus, for example, even a family can make do with a single measurement instrument 112 in which only the toys 128 have to be interchanged if child users are intended to use the measurement system 110.

FIGS. 4A and 4B show a front view (FIG. 4A) and a side view (FIG. 4B) of an alternative embodiment of a measurement instrument 112 which can be used within the scope of the measurement system 110 according to embodiments of the invention. In principle, this illustrated measurement instrument 112 is configured in a similar fashion to the measurement instrument 112 illustrated in the partial image at the bottom right of FIG. 1, and in turn comprises a housing 114 which likewise is designed in a similar fashion to the housing 114 illustrated in FIG. 1. Furthermore, a display element 116 and an application opening 124 are likewise included. In particular, the side view in accordance with FIG. 4B shows that the housing 114 can be designed ergonomically by appropriate grip elements 138 in order to make problem-free handling by a user possible, even outside of the measurement system 110. As a result of this, the measurement instrument 112 has an appealing design, even for users who wish to use the measurement instrument 112 without a toy 128.

Figure 5:
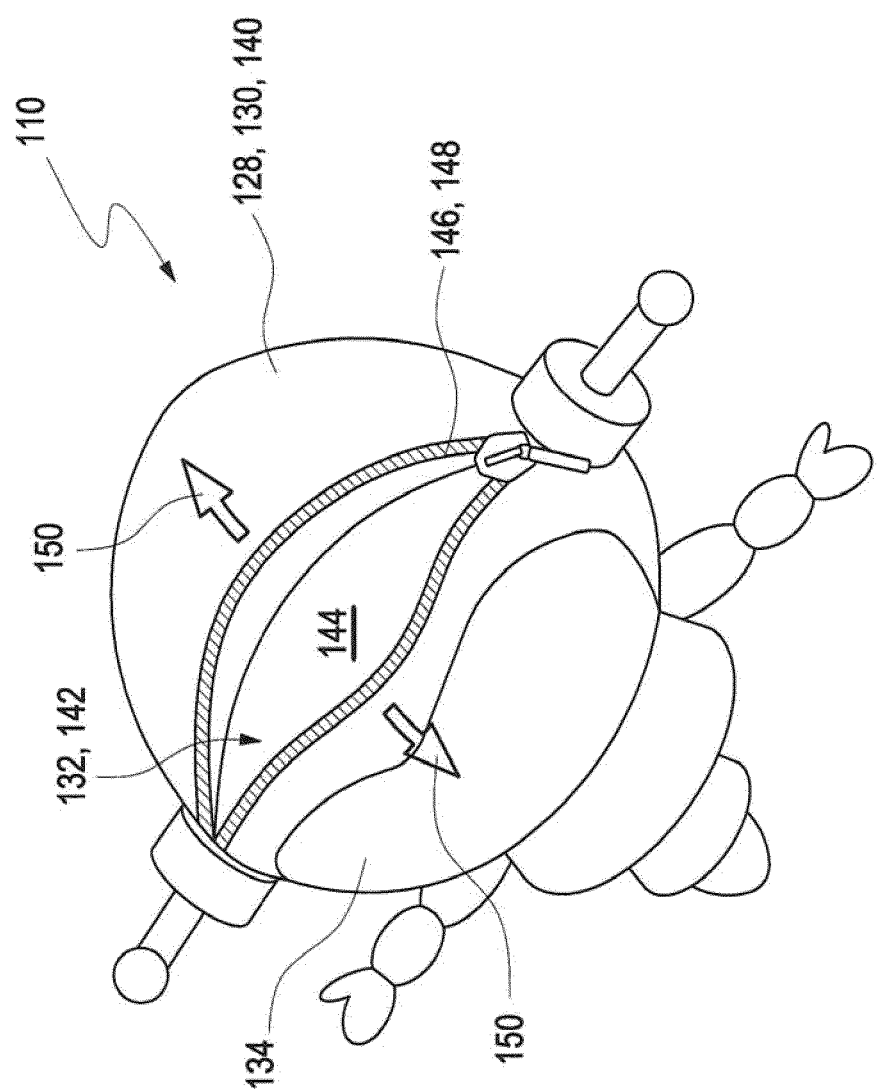
FIG. 5 shows a schematic illustration of a receptacle in a toy for a measurement system according to the invention.
Figure 6:
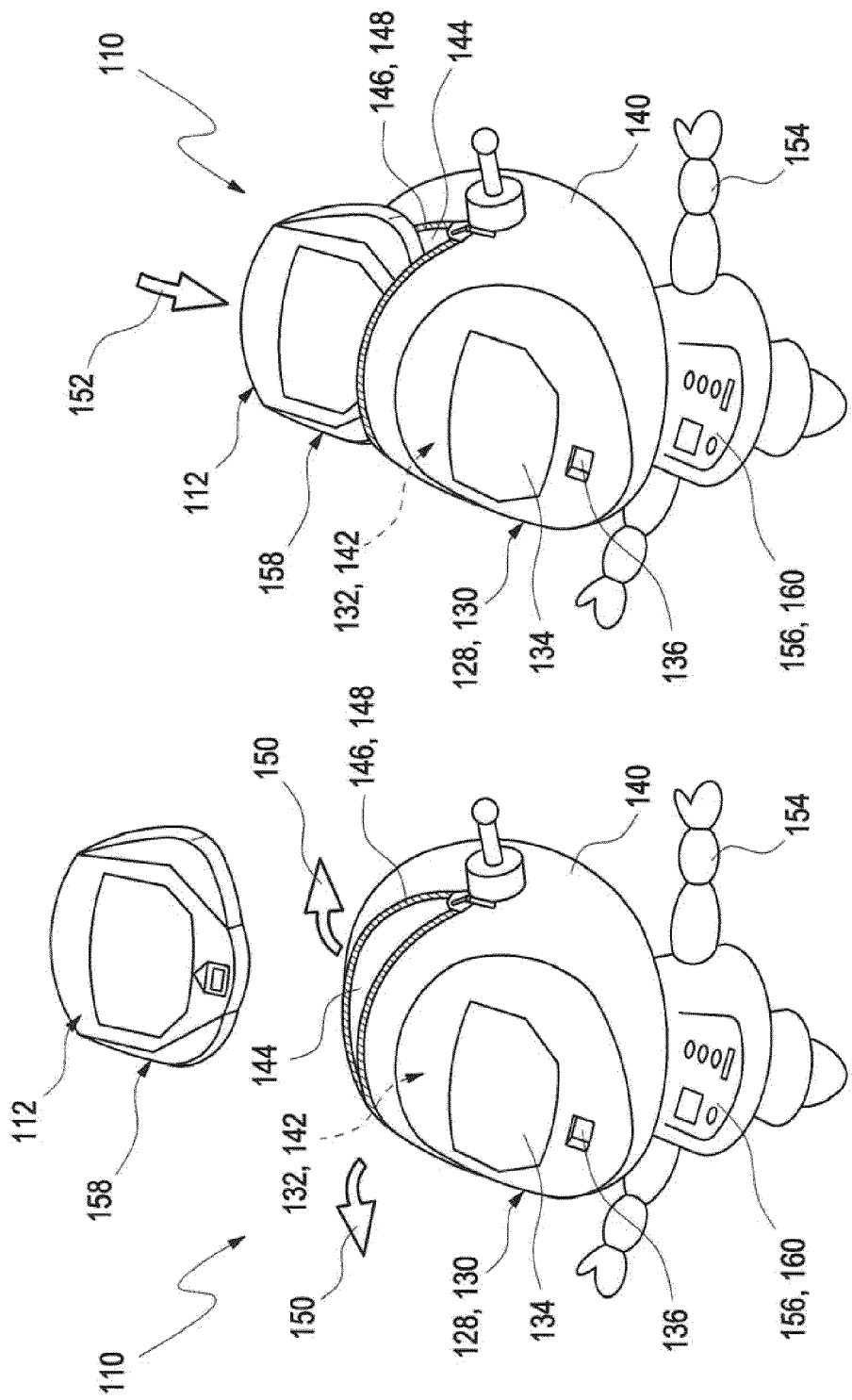
FIGS. 6A and 6B show a schematic illustration of a measurement instrument being held in a toy as per FIG. 5.

FIGS. 5 and 6A and 6B are intended to be used to explain an exemplary embodiment of a possible measurement system 110, a toy 128 which can be used in the measurement system 110, and a method for producing the measurement system 110. In this exemplary embodiment, the toy 128 again has a toy cover 130 which, by way of example, is in turn designed as a fantasy figure, as can be seen obliquely from above in the perspective illustration in accordance with FIG. 5. However, other refinements are also feasible.

In the illustrated exemplary embodiment, the figure has a head 140. The receptacle 132 previously described above is arranged within this head 140. However, a different arrangement of this receptacle 132 is, in principle, also feasible. Here, the receptacle 132 comprises a receptacle space 142 within the interior of the head 140, within which space the measurement instrument 112 can at least be held in part. This receptacle space 142 is provided by the mentioned opening 134 which can also be wholly or partly covered by e.g. a transparent material, e.g. a transparent sheet protector, in order to make visual access to the display element 116 possible in this exemplary embodiment. This can ensure additional protection for the display element 116. However, the opening 134 can alternatively also be completely uncovered because in general the housing 114 of the measurement instrument 112, which can also comprise the display element 116 and/or a transparent cover of this display element 116, can already provide sufficient protection.

The receptacle 132 and the receptacle space 142 have at least one receptacle opening 144. In this case, this at least one receptacle opening 144 is configured as a slot along a top side of the head 140 in the illustrated exemplary embodiment. In one embodiment, this receptacle opening 144 has at least one closing element 146 by means of which the receptacle opening 144 can be closed for use and opened or closed for inserting and/or removing the measurement instrument 112. This closing element 146 can, for example, comprise a zipper 148, as illustrated symbolically in FIGS. 5, 6A and 6B. However, alternatively, or additionally, different types of closing elements 146 can also be used, such as hook and loop fasteners, pushbuttons, textile buttons or the like. Generally, a user should be able to easily open the closing element 146, with, however, it also being possible for provision to be made for e.g. a child-proof lock to prevent an undesired removal of the measurement instrument 112 by a child patient.

FIGS. 6A and 6B indicate an embodiment of a simple production method for producing the measurement system 110. In a first partial step, the closing element 146 is opened in FIG. 6A (indicated by the arrows 150), and in a second partial step illustrated in FIG. 6B, the measurement instrument 112 is inserted into the receptacle 132 (indicated by reference symbol 152).

The toy 128 can be designed as a purely passive toy. Such a refinement is advantageous particularly when used by infants. However, the toy 128 can alternatively have a more complex functionality and carry out at least one toy-specific function. This function can for example comprise a communication function and/or a movement function (e.g. moving the arms 154 in FIGS. 6A and 6B) or the like. The toy 128 can for example comprise a toy control 156, indicated schematically in FIGS. 6A and 6B, in order to actively control this toy function. This toy control 156 can for example comprise one or more electronic components, e.g. one or more microprocessors. In the process, the toy control 156 can be configured to communicate with a control of the measurement instrument 112 via one or more interfaces not illustrated in the figures. The control of the measurement instrument 112 is referred to symbolically in FIGS. 6A and 6B by the reference symbol 158. This control 158 can in turn also for example comprise one or more electronic components, e.g. one or more microprocessors. Like in the toy control 156, the control 158 can also optionally comprise one or more memory storage elements, e.g. volatile and/or non-volatile memory storage. This makes it possible for data and/or control commands to be interchanged between, for example, the control 158 and the toy control 156 via the interface. In this fashion, the toy functionality can for example be coordinated and/or synchronized with the functionality of the measurement instrument 112, for example in order to display a facial expression on the display element 116 in a synchronized fashion in accordance with the functionality of the toy 128.

Furthermore, it is possible for the toy 128 to comprise an identifier 160, optionally also independently of the toy control 156, which identifier 160 is only indicated in FIGS. 6A and 6B and which can for example be wholly or partly integrated into the toy control 156 or can be held independently thereof in the toy 128. By way of example, the identifier 160 can be configured as an RFID chip. Accordingly, the measurement instrument 112 can be configured to read out at least one item of information from the identifier 160. This can for example be effected by an appropriate reader which is not illustrated in the figures. This reader can also be wholly or partly incorporated in the interface.

In accordance with the read out information about the toy 128, the measurement instrument 112 or the control 158 can be configured to adapt at least one function of the measurement instrument to the read out information. By way of example, the information can comprise an item of information regarding a type of toy 128 such that for example the correct set can be selected from a plurality of stored parameter sets of character parameters. This selection can correspond to the respectively used figure of the toy 128 or the type of toy 128. By way of example, read out and selection can be effected automatically in this case and therefore no additional user input is required when the measurement instrument 112 is inserted into a toy 128 in accordance with FIGS. 6A and 6B.

Figure 7:
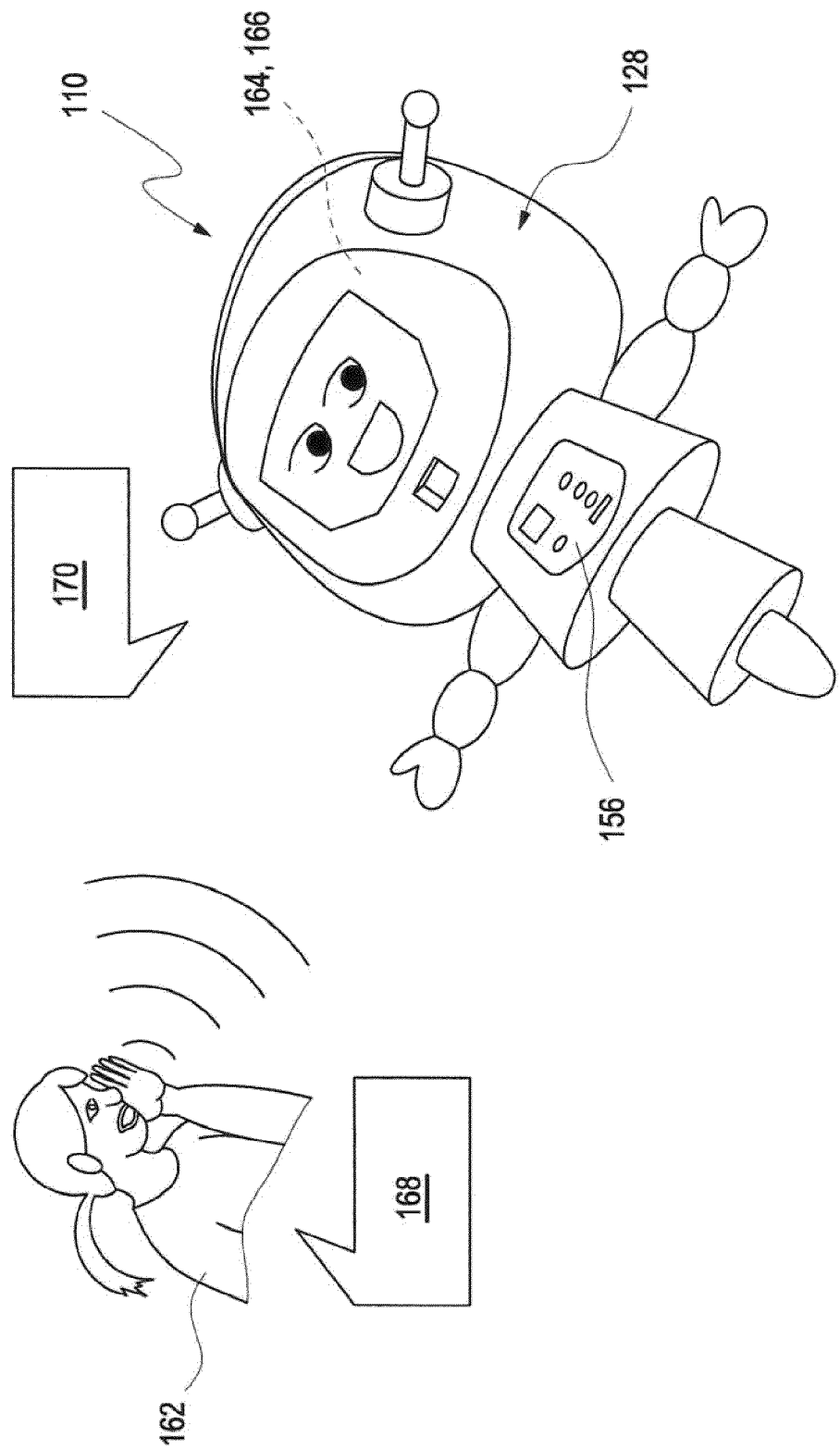
FIG. 7 shows an exemplary embodiment of a call and reply interaction between user and measurement system.
Figure 8:
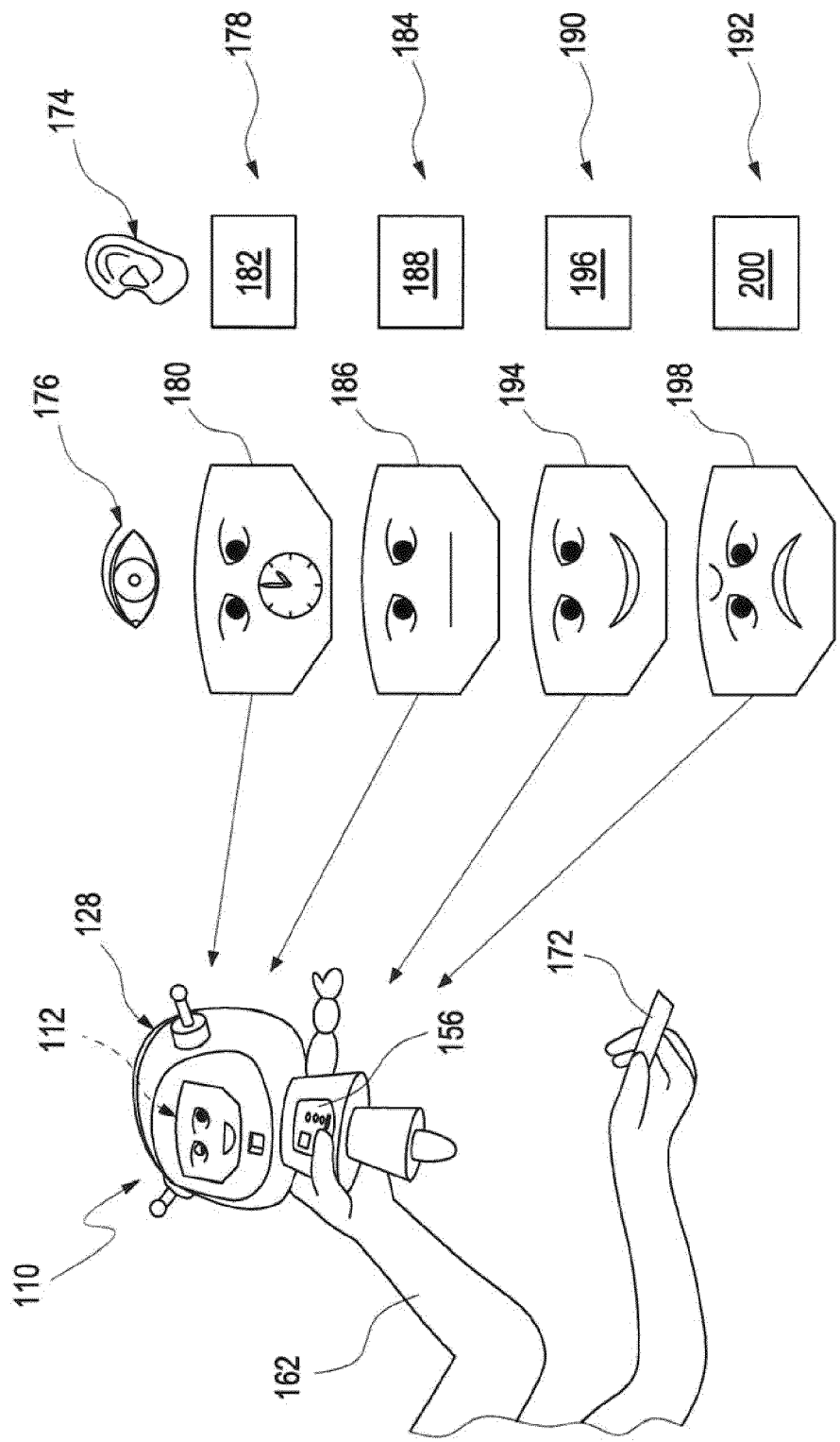
FIG. 8 shows a schematic illustration of possible visual and acoustic displays of a measurement system.

The measurement system 110 can be designed to interact with a user in different ways. Examples of such a user interaction are illustrated in FIGS. 7 and 8. Thus, FIG. 7 shows an exemplary embodiment of an interaction between a measurement system 110 and a user 162, for example a patient or another person. In general, reference is made to the fact that within the scope of the present description, the term patient does not necessarily imply a diseased state and so the patient can for example also be a person or an animal carrying out a screening examination. Furthermore, no distinction is made between the terms patient and user 162 either and so these can be different beings or identical beings. The measurement system 110 in the exemplary embodiment in accordance with FIG. 7 can for example be designed as described in the preceding exemplary embodiments and so, for example, reference can be made to the above description for possible refinements of this measurement system 110 and the measurement instrument 112 held therein, as well as the toy 128.

However, the measurement system 110 additionally comprises an input system 164 for inputting acoustic signals and an output system 166 which can also be configured for outputting acoustic signals; this can optionally also be the case in the preceding exemplary embodiments. This input system 164 and the output system 166 are in this case symbolically assigned to the measurement instrument 112 in the exemplary embodiment in accordance with FIG. 7. By way of example, the measurement instrument 112 can have one or more microphones as an input system 164 and/or one or more loudspeakers as an output system 166. However, alternatively, or additionally, one or both of the systems 164, 166 can also be wholly or partly assigned to the toy 128, e.g. the toy control 156.

The refinement of the measurement system 110 with the input system 164 and the output system 166 for example makes a search call by the user 162 possible; this is symbolically referred to by reference symbol 168 in FIG. 7. Thus, this search call 168 can for example comprise a simple calling out of a description of the measurement system 110 and/or of the toy 128. Thus, the measurement system 110 and/or the toy 128 can be provided with a name predetermined by a user and/or the producer; this is usually advantageous for increasing the acceptance of infant users 162, e.g. it can be called "Buddy". Thus, the search call 168 can for example comprise simple calling out of the term "Buddy" and/or a more complex search request. e.g. "Buddy, where are you?"

The measurement system 110, in particular the control 158 and/or the toy control 156 can be configured to reply to this search call 168. This response is symbolically referred to in FIG. 7 using the reference symbol 170. Again, there are a number of exemplary possibilities for this response 170, e.g. in the form of a speech output. However, alternatively, or additionally, other signals can also be emitted, including acoustic signals such as a buzzing, a signal tone or the like. However, for the purpose of increasing the acceptance as well, a speech output can be provided, for example in the form of a reply 170 "Hey-hey, I am here!" However, the interaction with the user 162 illustrated in FIG. 7 is only one of many possible exemplary possibilities, with numerous further exemplary possibilities being possible.

FIG. 8 symbolically illustrates an interaction with a user 162 which specifically relates to the measurement function of the measurement instrument 112. However, alternatively, or additionally, this interaction can in turn be wholly or partly implemented in additional components of the measurement system 110, in particular in components of the toy 128, e.g. once again in the toy control 156. Once again, a measurement system 110 is illustrated which can for example be in turn correspond to the previously described measurement systems 110. However, in principle, a different refinement is also possible. In this exemplary embodiment, the measurement system comprises a measurement instrument 112, e.g. in accordance with the above description, which for example is based on using one or more test elements 172 for the qualitative and/or quantitative detection of the at least one analyte in the liquid sample.

Here, the right-hand side of the illustration in FIG. 8 shows different signals which can be output by the measurement system 110 for supporting the measurement function. Here, the interaction with the user can for example be effected by means of acoustic signals, as illustrated in the right-hand side of the illustration in FIG. 8, which acoustic signals are symbolically referred to by reference symbol 174 in FIG. 8, and/or by means of optical signals, which are referred to symbolically by reference symbol 176 in FIG. 8. A combination of these signals is also possible.

Here, the reference symbol 178 refers to a first combination of acoustic and optical signals 174, 176 which can however also be implemented individually. In this first combination 178, the time is displayed 180, combined with e.g. an acoustic signal reminding about the necessity to carry out a measurement (reminder signal 182). For example, this reminder signal 182 can in turn comprise a speech output, e.g. the speech output: "okay, it's time for a measurement!"

Acoustic and optical signals 174, 176, which again can be implemented individually, are combined in a second combination 184. By way of example, this second combination 184 can be used while the measurement is being evaluated by the test element 172. This second combination 184 can for example comprise a wait display 186 as an optical signal 176 and/or an acoustic request to wait 188, e.g. again as a speech output, e.g. the request "one moment please!"

Furthermore, the right-hand half of the illustration in FIG. 8 shows a third combination 190 and a fourth combination 192, which output an evaluation of the measurement results. Thus, the third combination 190 can for example comprise a positive display 194 as an optical signal 176 and/or a positive acoustic evaluation 196. The positive acoustic evaluation 196 can again for example comprise speech output, e.g. the speech output "hey, great values today!" Hence, this third combination 190 can for example be used if the measurement results lie within a prescribed target range. The fourth combination 192 can accordingly be used to covey and/or evaluate negative measurement results, in particular measurement results outside of a target range. This fourth combination 192 can for example comprise a negative display 198 as an optical signal 176 and/or a negative acoustic evaluation 200 as an acoustic signal 174, e.g. again a speech output, e.g. the speech output "oh . . . a lot of sugar!"

Using this, a child-friendly user guide can be ensured, e.g. by means of the specified interactions and/or similar interactions. The optical and/or acoustic signals 176, 174 can in this case be adapted specifically to the utilized toy 128, for example by the optical signals 176 adapting a facial expression corresponding to the toy 128. Alternatively, or additionally, a voice of a speech output of the acoustic signals 174 can be adapted. Numerous further embodiments of this interaction are possible, e.g. intermediate values between the positive situation represented by the third combination 190 and the negative situation represented by the fourth combination 192. Overall, this interaction can significantly increase the acceptance of the measurement system 110.

Figure 9:
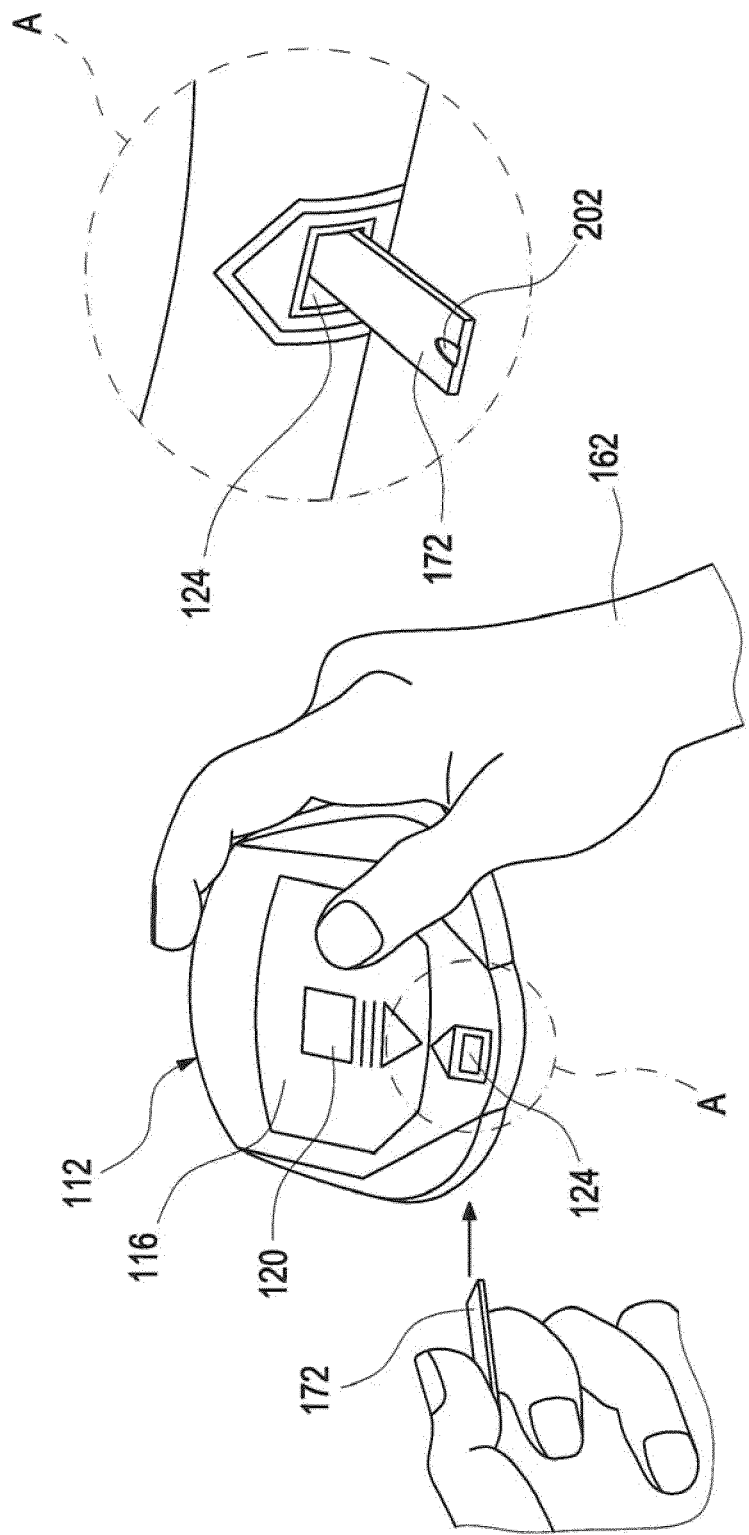
FIG. 9 shows an example of inputting a test strip into an input opening of a measurement instrument.

FIG. 9 once again illustrates in an exemplary fashion a possible use of the measurement instrument 112 without the toy 128. Use with the toy 128 can follow analogously. By way of example, the measurement instrument 112 can be configured in accordance with the above description. However, in principle, other refinements are also possible. The measurement instrument 112 again comprises an application opening 124, the region around which is illustrated again in an enlarged fashion in the partial image in the top right of FIG. 9 (referred to by the letter A). A user 162 pushes a test element 172 into the application opening 124. This test element 172, which can for example be configured as an optical and/or electrochemical test element, in particular as a test strip, can then comprise an application point 202 which is only indicated symbolically in FIG. 9 and onto which a liquid sample, e.g. a drop of blood, can be applied. After the application, the measurement instrument 112 can for example automatically and/or on the user's 162 command carry out a detection of the analyte in the liquid sample.

Numerous further possibilities for the interaction between the measurement instrument 112 and the test element 172 are feasible. Thus, the test element 172 can for example also be wholly or partly stored in the measurement instrument 112, and can be wholly or partly displaced outwards through the application opening 124 for applying the liquid sample. Again alternatively, or additionally, the application opening 124 can however also comprise a simple opening which unblocks a test region of the test element 172 for a user such that placement of the sample is possible. Numerous further refinements are feasible.

Figure 10:
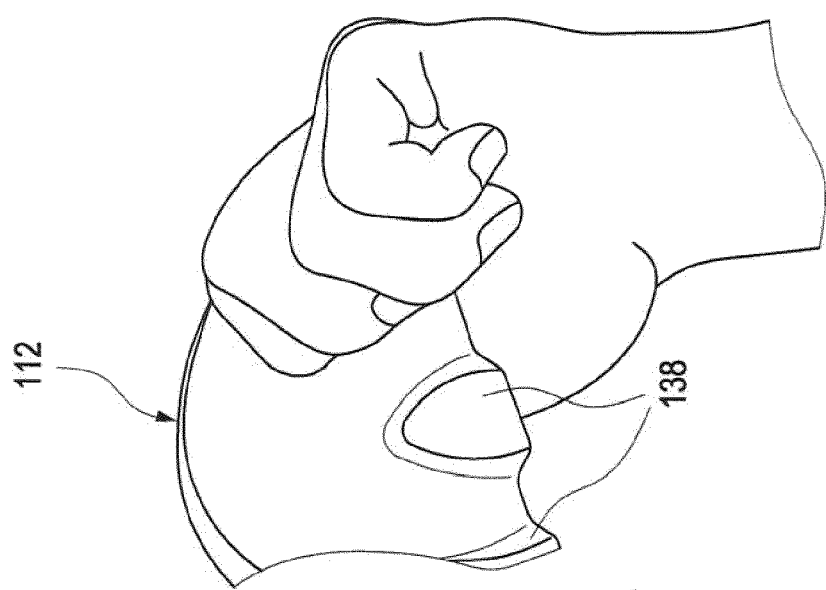
FIGS. 10A and 10B show different views of the use of an exemplary measurement instrument independently of the measurement system.
Figure 10:
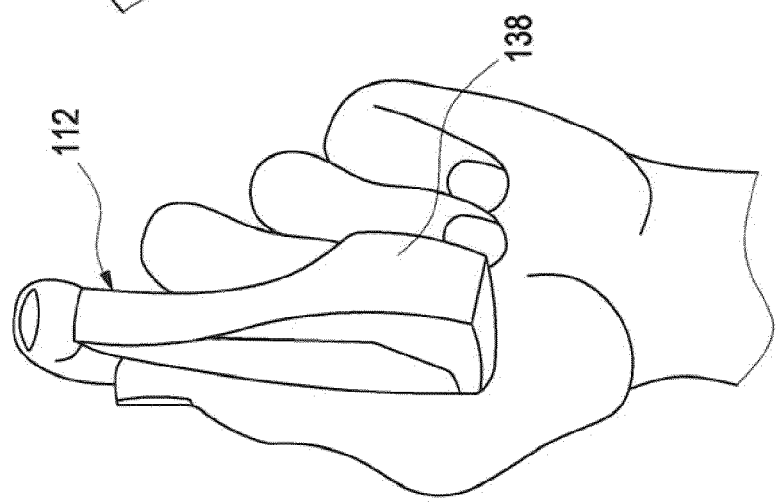

FIGS. 10A and 10B illustrate a further exemplary embodiment of a measurement instrument 112, in a side view (FIG. 10A) and a back view (FIG. 10B), which can likewise be used within the scope of the measurement system 110 according to the invention. With respect to the ergonomic design, the measurement instrument 112 differs slightly from the exemplary embodiment in accordance with FIGS. 4A and 4B; however, there are similarities. The measurement instrument 112 again comprises grip elements 138 which make handling the measurement instrument 112 easier. Hence, the measurement instrument 112 can for example be used independently of the measurement system 110. However, these grip elements 138 can be used with synergetic effect to stabilize a hold of the measurement instrument 112 in the toy 128.

Figure 11:
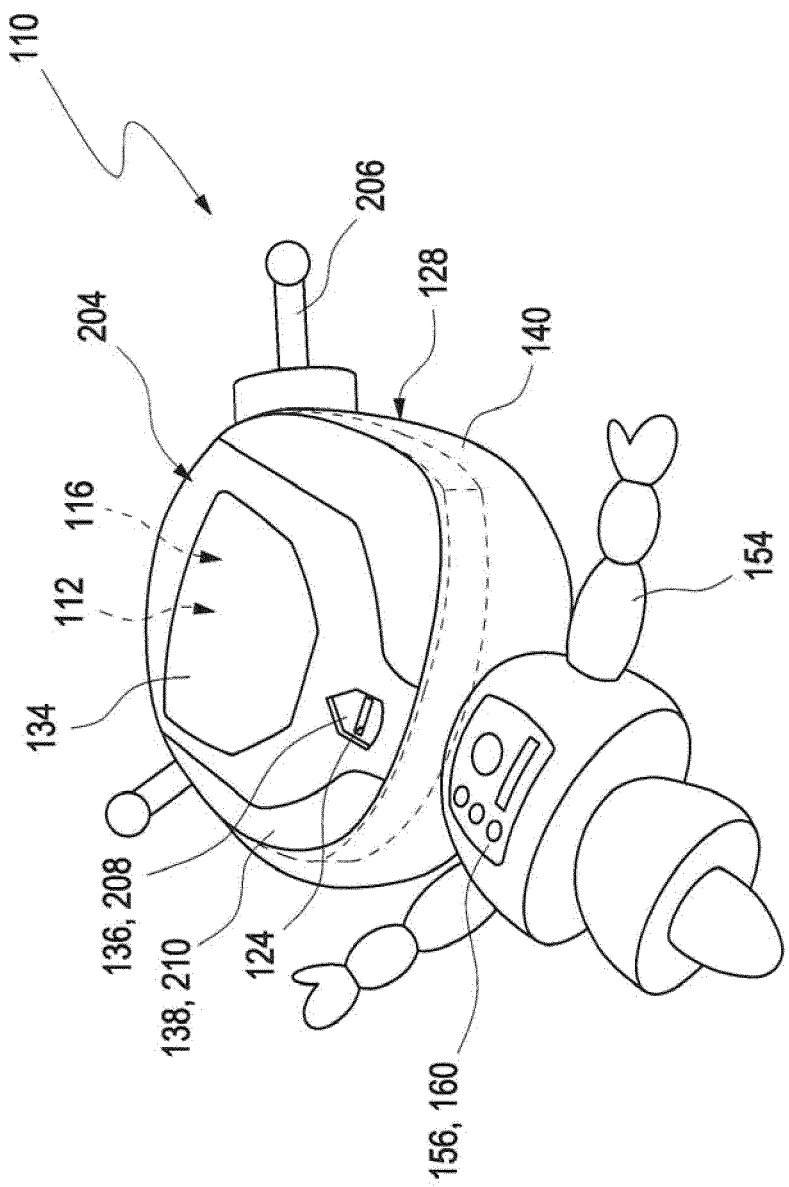
FIG. 11 shows a perspective illustration of an embodiment of the measurement system.

FIG. 11 once again illustrates the measurement system 110 in accordance with the above-described exemplary embodiments in an enlarged perspective view. For the details of this exemplary embodiment, reference can be made, for example, to the description of the above exemplary embodiments, for example the exemplary embodiments of FIG. 1, 2 or 6A and 6B. The perspective illustration of FIG. 11 in particular affords the possibility of recognizing the particularly illustrated design of the toy 128 as an exemplary figure. By way of example, it can be seen in this case that a head 140 of the toy 128 can be designed such that said head can have a pronounced facial region 204 for example in addition to additional elements of the head such as ears 206. It is in this facial region 204, which for example can comprise the openings 134, 136, that the main interaction of the measurement instrument 112 and the toy 128 can take place such that the functions of the measurement instrument 112 and those of the toy 128 complement each other to form the measurement system 110. Thus, as described above, the facial region 204 can for example be, in full or in part, of transparent design such that the display element 116 can be visible, for example through a transparent cover foil in the region of the opening 134. The application opening 124 can likewise be artistically integrated into the facial region 204 such that it is for example perceived as a "mouth" 208. It is also possible for further components of the measurement instrument 112 to be visible to a user from the outside. By way of example, regions of the grip elements 138 can also be perceived through a transparent cover as "cheeks". The described embodiments only constitute examples of how a commercially available measurement instrument 112 can be artistically integrated into the toy 128. Numerous further refinements are feasible.

Figure 12:
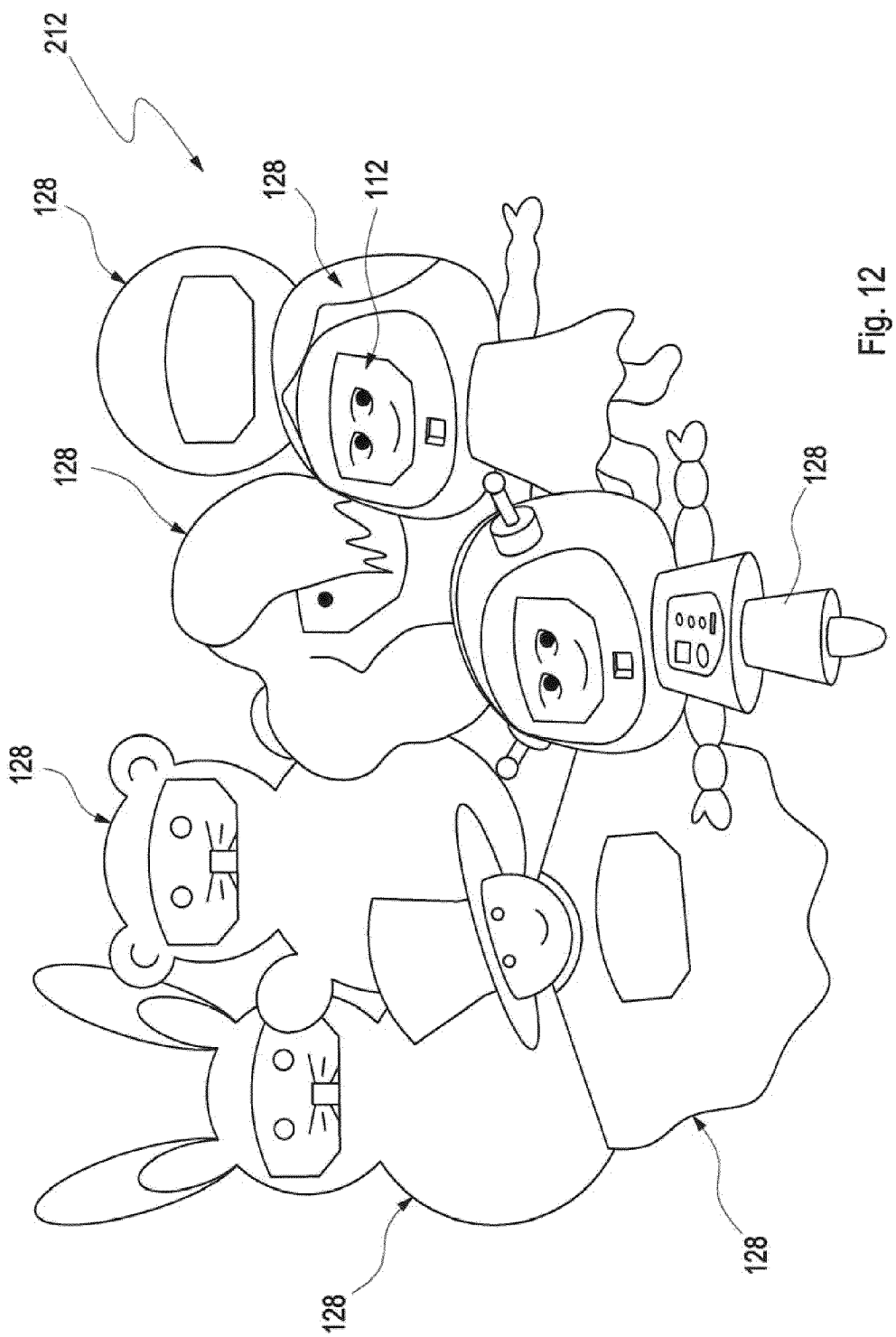
FIG. 12 shows an exemplary embodiment of a kit for a measurement system according to the invention.

Finally, FIG. 12 symbolically shows an exemplary embodiment of a kit 212 according to the invention. This kit 212 can on the one hand be used to produce a measurement system 110 according to the invention, but it can also be used by a user as a kit for detecting one or more analytes in a bodily fluid.

In addition to one or more measurement instruments 112, the kit comprises a plurality of toys 128 in different embodiments. Only a single measurement instrument 112 is indicated in FIG. 12. Each of the toys 128 is configured to hold one measurement instrument 112, for example in accordance with the embodiments described above on the basis of FIGS. 5 and 6A and 6B.

However, the toys 128 differ in their outer appearances. Thus, the kit 212 can for example comprise a plurality of dolls, fantasy figures and/or toy animals, in particular soft toys or similar toys 128. In principle, integration into toys 128 which are not ascribed their own character by the child's fantasy is also possible.

The illustrated kit 212 can be utilized for different purposes. Firstly, such kits 212 simplify the production of a measurement system 110 according to the invention. The multiplicity of toys 128 can for example be stored with one or more defined types of measurement instrument 112 or instruments. Thus, a target group-specific measurement system 110 can be provided in a simple and cost effective manner and without much logistical complexity. Alternatively, or additionally, a kit 212 can however also be used by a user or a group of users 162, e.g. a family. This makes it possible to quickly adapt the outer appearances of the measurement systems 110 to the respective individual user 162 who is supposed to carry out a measurement. This also makes it possible to cut costs, and the user friendliness can be significantly increased.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A measurement system for detecting at least one analyte in a bodily fluid, comprising:
   (i) at least one measurement instrument configured for detecting the analyte in the bodily fluid using at least one test element on which the bodily fluid is to be placed, the measurement instrument being configured as a portable hand-held instrument and having a housing with at least one display element and at least one operating element, the measurement instrument further including at least one application opening configured to enable a placement of a sample of the bodily fluid on the test element when the test element is held in the application opening; and
   (ii) a toy having at least one receptacle for reversibly holding the measurement instrument, the receptacle including at least one fixing apparatus configured to fix the measurement instrument relative to the toy in the receptacle, the receptacle being configured such that if the measurement instrument is held by the receptacle, the sample can be placed on the test element and the display element and the operating element are accessible, at least in part, wherein the toy includes at least in part an outer cover for the measurement instrument that is configured as a human figure, an animal figure or a fantasy figure, with the receptacle having an opening, the opening being arranged at least in part in a facial region of the figure, the opening being configured such that the display element can at least in part be recognized in the opening when the measurement instrument is held in the receptacle and the measurement instrument is configured such that it can be used both in the measurement system and also independently of the toy.

2. The measurement system according to claim 1, in which the receptacle has at least one receptacle space, the measurement instrument being holdable at least in part within the receptacle space, with the receptacle furthermore having at least one closing element, the closing element being configured to secure the measurement instrument in the receptacle space when said closing element is in a closed state and to permit a removal of the measurement instrument from the receptacle when said closing element is in an opened state.

3. The measurement system according to claim 2, in which the closing element comprises at least one of the following elements: a zipper; a pushbutton; a textile button; and a lock which can be released by a user.

4. The measurement system according to claim 1, in which the measurement instrument furthermore has at least one acoustic element, the acoustic element being configured to output acoustic signals.

5. The measurement system according to claim 4, in which the output of acoustic signals comprises speech output comprising one or more of the following functions: an output of at least one measurement result of the detection of the analyte in the bodily fluid; a statement regarding at least one measurement result of the detection of the analyte in the bodily fluid; a request to undertake a measurement; a request to undertake at least one action; and a reply to a search call of a user.

6. The measurement system according to claim 1, in which the measurement instrument comprises at least one input element for inputting acoustic signals.

7. The measurement system according to claim 1, in which the measurement instrument has at least one memory storage element, with a plurality of sets of character parameters from different types of toys being stored in the memory storage element, wherein a certain record is selectable from the memory storage element in accordance with the particular toy.

8. A measurement system for detecting at least one analyte in a bodily fluid, comprising:
   (i) at least one measurement instrument for detecting the analyte in the bodily fluid, the measurement instrument being configured as a portable hand-held instrument and having a housing with at least one display element; and
   (ii) a toy having at least one receptacle for reversibly holding the measurement instrument, the receptacle being configured such that if the measurement instrument is held by the receptacle, the display element is accessible, at least in part, and wherein the measurement instrument is configured such that it can be used both in the measurement system and also independently of the toy, in which the toy has at least one toy control, the toy control being configured to carry out at least one toy-specific function, the toy furthermore having at least one interface for interchanging data and/or control commands with the measurement instrument, wherein the toy control is configured to communicate with a control of the measurement instrument.

9. The measurement system according to claim 8, in which the measurement instrument furthermore has at least one operating element, the receptacle being configured such that if the measurement instrument is held by the receptacle, the operating element is accessible, at least in part.

10. The measurement system according to claim 8, in which the receptacle has at least one fixing apparatus, the fixing apparatus being configured to fix the measurement instrument relative to the toy.

11. The measurement system according to claim 8, in which the measurement instrument is configured to detect the analyte using at least one test element, the measurement instrument having at least one application opening, the application opening being configured to enable a placement of a sample of the bodily fluid on a test element held in the application opening, with the receptacle being configured such that the sample can be placed when the measurement instrument is held in the receptacle.

12. The measurement system according to claim 8, in which the toy is at least in part designed as a human figure, an animal figure or a fantasy figure, with the receptacle having an opening, the opening being arranged at least in part in a facial region of the figure, the opening being configured such that the display element can at least in part be recognized in the opening when the measurement instrument is held in the receptacle.

13. The measurement system according to claim 12, in which the measurement instrument has a control, the control being configured to display at least parts of a face of the figure on the display element in at least one mode of operation.

14. The measurement system according to claim 13, in which the control is configured to change a facial expression of the face according to one or more of the following conditions: a measurement result of the detection of the analyte in the bodily fluid; a time of a measurement result; and a time for a future measurement to be carried out.

15. The measurement system according to claim 8, in which the measurement instrument is configured to adapt at least one function to the toy.

16. A measurement system for detecting at least one analyte in a bodily fluid, comprising:
 (i) at least one measurement instrument for detecting the analyte in the bodily fluid, the measurement instrument being configured as a portable hand-held instrument and having a housing with at least one display element; and
 (ii) a toy having at least one receptacle for reversibly holding the measurement instrument, the receptacle being configured such that if the measurement instrument is held by the receptacle, the display element is accessible, at least in part, and wherein the measurement instrument is configured such that it can be used both in the measurement system and also independently of the toy, in which the toy has at least one identifier, the identifier having at least one item of information about the toy, the measurement instrument being configured to read out the identifier.

17. A toy for use in a measurement system, the toy comprising at least one toy cover which substantially determines the outer shape of the toy, the toy furthermore having at least one receptacle for reversibly holding a measurement instrument for detecting an analyte in a bodily fluid, wherein the toy cover is configured as a human figure, an animal figure or a fantasy figure, with the receptacle having an opening, the opening being arranged at least in part in a facial region of the figure, the measurement instrument being configured as a portable hand-held instrument and having a housing with at least one display element, the receptacle being configured such that if the measurement instrument is held by the receptacle, the display element is accessible, at least in part, and with the opening of the receptacle being configured such that the display element can at least in part be recognized in the opening when the measurement instrument is held in the receptacle.

18. A kit for detecting at least one analyte in a bodily fluid, the kit comprising at least one measurement instrument configured for detecting the analyte in the bodily fluid using at least one test element on which the bodily fluid is to be placed, each measurement instrument being configured as a portable hand-held instrument and having a housing with at least one display element and at least one operating element, the measurement instrument further including at least one application opening configured to enable a placement of a sample of the bodily fluid on the test element when the test element is held in the application opening, furthermore comprising a plurality of toys each having at least one receptacle for reversibly holding one of the measurement instruments, the receptacle including at least one fixing apparatus configured to fix the measurement instrument relative to the toy in the receptacle, each receptacle being configured such that if one of the measurement instruments is held by the receptacle, the sample can be placed on the test element and the display element and the operating element are accessible, at least in part, wherein the toy includes at least in part an outer cover for the measurement instrument that is configured as a human figure, an animal figure or a fantasy figure, with the receptacle having an opening, the opening being arranged at least in part in a facial region of the figure, the opening being configured such that the display element can at least in part be recognized in the opening when the measurement instrument is held in the receptacle, and each measurement instrument is configured such that it can be used both interchangeably in one of the toys and independently of the toys, and wherein each measurement instrument and respective one of the toys together form a child-friendly measurement system.

19. A method for producing a measurement system for detecting at least one analyte in a bodily fluid, comprising:
 selecting a measurement instrument configured to detect the analyte in the bodily fluid using at least one test element on which the bodily fluid is to be placed, the measurement instrument being configured as a portable hand-held instrument and having a housing with at least one display element and at least one operating element, the measurement instrument further including at least one application opening configured to enable a placement of a sample of the bodily fluid on the test element when the test element is held in the application opening;
 selecting a toy comprising at least one receptacle configured for reversibly holding the measurement instrument therein, the receptacle including at least one fixing apparatus configured to fix the measurement instrument relative to the toy in the receptacle, the receptacle being configured such that if the measurement is held by the receptacle the sample can be placed on the test element and the display element and the operating element of the measurement instrument are at least partially accessible, wherein the toy includes at least in part an outer cover for the measurement instrument that is configured as a human figure, an animal figure or a fantasy figure, with the receptacle having an opening, the opening being arranged at least in part in a facial region of the figure, the opening being configured such that the display element can at least in part be recognized in the opening when the measurement instrument is held in the receptacle; and
 placing the measurement instrument within the receptacle, wherein the measurement instrument is configured such that it can be used for detecting the analyte both after the placing step and before the placing step.

20. The method according to claim 19, further comprising placing a plurality of different types of toys in a storage, wherein the step of selecting a toy comprises selecting one of the types of toys based on a target group of users of the measurement system to be produced.

* * * * *